United States Patent [19]

Sharvit et al.

[11] Patent Number: 5,206,232
[45] Date of Patent: Apr. 27, 1993

[54] FUNGICIDAL IMIDAZOLE COMPLEXES

[75] Inventors: Joseph Sharvit, Lehavim; Daniel Shohat, Beer-Sheva; Yosef Gur, Omer, all of Israel

[73] Assignee: Makhteshim Chemical Works Ltd., Beer-Sheva, Israel

[21] Appl. No.: 662,650

[22] Filed: Mar. 1, 1991

[30] Foreign Application Priority Data

Mar. 5, 1990 [IL] Israel .................................... 93636
Feb. 7, 1991 [IL] Israel .................................... 97181

[51] Int. Cl.$^5$ ..................... A61K 31/555; C07F 3/06; C07F 7/22
[52] U.S. Cl. ..................... 514/184; 548/101; 548/109
[58] Field of Search .............. 548/101, 109; 514/184

[56] References Cited

U.S. PATENT DOCUMENTS 3,789,122  1/1974  Klopping ........................... 514/186
4,086,339  4/1978  Matolcsy et al. .................. 514/311
4,250,179  2/1981  Birchmore et al. ................ 514/184

Primary Examiner—Mary C. Lee
Assistant Examiner—Joseph K. McKane
Attorney, Agent, or Firm—Browdy and Neimark

[57] ABSTRACT

The present invention concerns improved crystalline metal complexes of the fungicide 1-[N-propyl-N-2-(2,4,6-trichlorophenoxy)-ethyl carbamoyl]-imidazole, known by the common name prochloraz, its improved formulations and their use in combatting fungi, especially powdery mildew (*Sphaerotheca fuliginia*) and coffee berry disease (*Colletotrichum coffeanum*).

11 Claims, No Drawings

FUNGICIDAL IMIDAZOLE COMPLEXES

BACKGROUND OF THE INVENTION

The present invention concerns an improved metal complexes of the fungicide 1-[N-propyl-N-2-(2,4,6-trichlorophenoxy)-ethyl-carbamoyl]-imidazole, known by the common name prochloraz, its improved formulations and their use in combating fungi, especially powdery mildew (*Sphaerotheca fuliginia*) and coffee berry disease (*Colletotrichum coffeanum*).

Prochloraz is a protectant and eradicant fungicide, effective against a wide range of diseases affecting field crops, fruit, turf and vegetables. Its use was first reported in United Kingdom patent numbers 1,469,772 and 1,576,277, whose contents are incorporated by their mention. Prochloraz is sold under two different types of formulation. One form is an emulsifiable concentrate, which contains the free compound as active ingredient. The second formulation is a wettable powder where the active ingredient is in the form of a metal complex. The metal complexes of prochloraz were first reported in United Kingdom patent number 1,567,521 (Israel patent no. 54,304), whose contents are incorporated by its reference.

The metal complexes of prochloraz were intended to solve two problems found in using the free, non-complexed prochloraz. The first was, that non-complexed prochloraz was found difficult to handle and formulate on a solid powder carrier. It was found necessary to first absorb it on a carrier prior to preparing a powder, causing loss of material, lowering the fungicidal activity and preventing the preparation in a highly concentrated form. The second problem was that free, non-complexed prochloraz was found to be phytotoxic to some crops. However, the metal complexes of prochloraz were found to avoid these problems. Thus the metal complexes of prochloraz, generally were found to be solid, distinctly melting compounds, readily formulated with a solid carrier or concentrate, without the phytotoxic problems found on susceptible crops.

Patent coverage on the metal complexes of prochloraz was obtained in many countries (i.e. GB 1,567,521 and U.S. Pat. No. 4,250,179). The metals exemplified or disclosed were divalent metals such as copper, manganese, iron, nickel and cobalt. Nowhere were metal salts of $SnCl_2$ or $ZnCl_2$ with prochloraz disclosed or claimed. Indeed, there are indications from the prior art that these specific salts cannot be prepared. With regard to the cobalt complex, while it was disclosed, it was not claimed, nor was this complex exemplified. Thus, the present invention is a selection patent of those patents covering metal complexes of prochloraz.

OBJECTIVES OF THE INVENTION

It is the objective of the present invention to provide crystalline metal complexes of prochloraz with $SnCl_2$, $ZnCl_2$, or $CoCl_2$. It is an objective of the present invention to also provide a formulation of these complexes, which can be readily formulated as a wettable powder. A further objective is the provision of formulations of the complexes having unusual and unexpected fungicidal activity, especially against powdery mildew and coffee berry disease. These and other objectives of the invention will become apparent to those skilled in the art from the following description.

SUMMARY OF THE INVENTION

In accordance with the present invention, there is provided crystalline metal complexes of prochloraz having the formula:

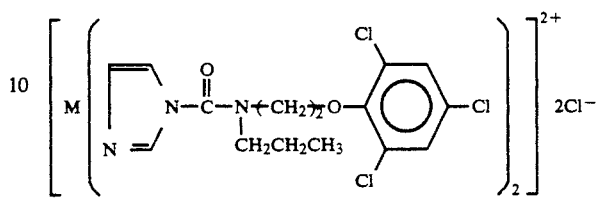

wherein M is zinc, tin or cobalt.

The metal complexes produced by this invention are crystalline solids having sharp, definite melting points and defined compositions. This enables them to be easily handled and formulated as wettable powders.

The present invention also provides an improved method of controlling fungi, especially powdery mildew, applying to the infested material or plant a composition containing an effective amount of one of these metal complexes.

DETAILED DESCRIPTION OF THE INVENTION

The complex containing zinc is a white crystalline solid having a melting point of 100° C.–102° C. Analysis of its zinc content showed 7.29% zinc compared to a value of 7.35%, which correlates with a complex containing one molecule of $ZnCl_2$ per molecule of prochloraz. The complex containing tin is a white crystalline solid having a melting point of 95° C. Analysis of its tin content showed 7.99% tin, which correlates with a complex of one molecule of $SnCl_2$ per two molecules of prochloraz. The complex containing cobalt is a white crystalline solid having a melting point of 136° C. 138° C. Analysis of its cobalt content showed 6.68% cobalt, which correlates with a complex of one molecule of $CoCl_2$ per two molecules of prochloraz.

The nuclear magnetic resonance spectrum of these complexes in solution showed a definite shift in the singlet hydrogens belonging to the imidazole group. This shows complexation, and that the complexation takes place on the imidazole group. Details of the spectrum are shown in Table 1.

These complexes are prepared by adding a water solution of $SnCl_2$, $ZnCl_2$ or $CoCl_2$ to a clear alcoholic solution of prochloraz in a molar ratio of 1:2 metal salt to prochloraz. While most common alcohols give good results, alcohols such as ethanol or isopropanol were found to be preferred.

The reaction temperature is conveniently chosen within the range of from 10° C. to 60° C., preferably room temperature.

According to a further feature of the invention, there is provided a fungicidal composition which comprises a compound of the invention together with a carrier. The active compound can be employed as a wide variety of formulations, for example as an aqueous dispersion, a dispersible powder, a seed dressing, granules or dust.

As a dispersion the composition comprises an active compound together with a dispersing agent dispersed in a liquid medium, preferably water. It can be in the form of a concentrated primary composition which requires dilution with a suitable quantity of water or other diluent before application. Such primary compositions are a convenient way of supplying the consumer and a preferred example is a dispersible powder. A dispersible powder comprises an active compound, a dispersing agent and a solid carrier. The latter can be, for example, kaolin, talc, or diatomaceous earth and, in addition, the dispersible powder can contain a wetting agent.

Other formulations include seed dressings, granules or dusts, in all of which the active compound is associated with a solid carrier and which are intended for direct application. They can be made by methods well known in the art. Preferably all compositions comprising a solid carrier are made by mixing the active compound in particulate form with a particulate carrier.

TABLE 1

PROTON MAGNETIC SPECTRA OF PROCHLORAZ AND ITS METAL COMPLEXES

|  | Prochloraz[a] | Zn Complex of Prochloraz |
|---|---|---|
| Triplet | 0.93 (3H) | 0.95 (3H) |
| Quartet | 1.75 (2H) | 1.76 (2H) |
| Triplet | 3.55 (2H) | 3.54 (2H) |
| Triplet | 3.87 (2H) | 3.85 (2H) |
| Triplet | 4.22 (2H) | 4.20 (1H) |
| Singlet | 7.11 (1H) | 7.29 (1H) |
| Singlet | 7.31 (1H) | 7.32 (2H) |
| Singlet | 7.32 (2H) | 7.47 (1H) |
| Singlet | 7.96 (1H) | 8.41 (1H) |

[a] = In ppm.

The concentration of the active compound in the composition of the invention can vary widely. In the case of a primary composition it is preferably from 15% to 95% by weight, more especially from 50% to 80% by weight. A composition intended for direct application to a crop preferably comprises from 0.001% 10 10%, more especially from 0.005% to 5% by weight of the active compound, although the aerial spraying of a crop is contemplated compositions having a higher concentration, for example up to 30% by weight may be chosen in preference.

Also included in the invention is a method for controlling a phytopathogenic fungus which comprises applying to seeds, plants or their habitat a compound of the invention. For convenience and effectiveness it is preferred to apply the active compound in the form of a composition as described above.

In the method of the invention the compound is applied to seeds, plants or their habitat. Thus the active compound can be applied directly to the plant by, for example, spraying or dusting either at the time when the fungus has begun to appear on the plant or before the appearance of the fungus as a protective measure. In both such cases the preferred mode of application is by foliar spraying. It is generally important to obtain good control of fungi in the early stages of plant growth as this is the time when the plant can be most severely damaged. For cereal crops such as wheat, barley and oats, it is often desirable to spray the plant at or before growth stage 5 (Feeke's Scale) although additional treatments by spraying when the plant is more mature can augment resistance to the growth or spread of fungi.

Sometimes it is practicable to treat the roots of a plant before or during planting, for example by dipping the roots in a suitable liquid or solid composition. When the active compound is applied directly to the plant. A suitable rate of application is from 0.01 to 10 kilograms per hectare.

Alternatively, the compound can be applied directly to the soil at the same time as drilling, so that the presence of active compound in the soil controls the growth of fungi which attack the seed. When the soil is treated directly, the active compound can be applied in any manner which allows it to be intimately mixed with the soil by applying the active ingredient at the same time as drilling, inserting it in the same drill as the seed. A suitable application rate is within the range of from 0.1 to 10 kilograms per hectare.

In a further method of the invention, the active compound an be applied to the seed as a dressing in order to combat seed-borne diseases. This method is of particular use in the treatment of cereal grain against attack by, for example, leaf spot of oats and leaf stripe of barley. When the cereal grain is stored in a store-room or container, the store-room or container can be treated with the active compound instead of or in addition to the treatment of the ceral grain itself. A suitable rate of application for a seed dressing is from 0.05 to 5 grams per kilogram, such as for example from 0.1 to 1 grams per kilogram.

A more particular method of the invention is one for controlling fungal diseases on a cereal crop, such as for example wheat, barley, oats, or rye, which comprises applying to the crop a compound of the invention. For any particular compound it is necessary to choose the most effective method from amongst those described above at a suitable rate of application ensuring fungus control.

The crystalline metal complexes of prochloraz of the present invention showed particularly good results against powdery mildew and coffee berry disease, especially when compared to the results of known commercial metal complexes of prochloraz.

While the invention will now be described in connection with certain preferred embodiments in the following examples it will be understood that it is not intended to limit the invention to these particular embodiments. On the contrary, it is intended to cover all alternatives, modifications and equivalents as may be included within the scope of the invention as defined by the appended claims. Thus, the following examples which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

EXAMPLE 1

PREPARATION OF THE TIN COMPLEX OF PROCHLORAZ

To a stirred, homogeneous solution of 80 g prochloraz in 500 ml ethanol or isopropanol kept at room temperature was added dropwise over a period of thirty minutes a solution of 225 g $SnCl_2$ in 100 ml water. The resulting mixture was stirred for a further two hours and the resulting crystals filtered, rinsed with water and ethanol or isopropanol (depending on the solvent originally used) to afford a white crystalline powder having a melting point of 95° C.

EXAMPLE 2

PREPARATION OF THE ZINC COMPLEX OF PROCHLORAZ

To a stirred homogeneous solution of 80 g prochloraz in 500 ml ethanol or isopropanol kept at room temperature, was added dropwise over a period of thirty minutes a solution of 13.6 g $ZnCl_2$ in 20 ml water. The resulting mixture was stirred for a further 2.5 hours and the resulting crystals filtered, washed with water and alcohol to afford a white crystalline powder having a melting point of 100° C.-102° C.

Elemental analysis: Zinc: 7.35% calculated, 7.29% found; Chloride: 7.97% calculated, 8.02% found.

EXAMPLE 3

PREPARATION OF THE COBALT COMPLEX OF PROCHLORAZ

Following the method of Example 1 but using $CoCl_2$, the white crystalline $CoCl_2$ complex of prochloraz was prepared. Its melting point was 136° C.-138° C.

EXAMPLE 4

PREPARATION OF A WETTABLE POWDER FORMULATION OF THE ZINC CHLORIDE COMPLEX

A wettable powder formulation was prepared by mixing together the following ingredients:

| | |
|---|---|
| Bis-[1-{N-propyl-N-2-(2,4,6-trichlorophenoxy)-ethyl-carbamoyl}-imidazole]-zinc chloride complex | 54% |
| Sodium lignosulfonate (as dispersant) | 3% |
| Wettol NT-1 (wetting agent) | 2% |
| Wessalon (precipitated silica carrier) | 5% |
| Kaolin | to complete to 100% by weight |

EXAMPLE 5

PREPARATION OF A WETTABLE POWDER FORMULATION OF THE TIN (II) CHLORIDE COMPLEX

A wettable powder formulation was prepared by mixing together the following ingredients:

| | |
|---|---|
| Bis-[1-{N-propyl-N-2-(2,4,6-trichlorophenoxy)-ethyl-carbamoyl}-imidazole]-tin(II) chloride complex | 54% |
| Sodium lignosulfonate (as dispersant) | 3% |
| Wettol NT-1 (wetting agent) | 2% |
| Wessalon (precipitated silica carrier) | 5% |
| Kaolin | to complete to 100% by weight |

EXAMPLE 6

PREPARATION OF A WETTABLE POWDER FORMULATION OF COBALT(II) CHLORIDE COMPLEX

A wettable powder formulation was prepared by mixing together the following ingredients:

| | |
|---|---|
| Bis-[1-{N-propyl-N-2-(2,4,6-trichlorophenoxy)-ethyl-carbamoyl}-imidazole]-cobalt (II) chloride complex | 51% |
| Sodium lignosulfonate (as dispersant) | 3% |
| Wettol NT-1 (wetting agent) | 2% |
| Wessalon (precipitated silica carrier) | 5% |
| Kaolin | to complete to 100% by weight |

EXAMPLE 7

FUNGICIDAL ACTIVITY OF THE COMPLEXES AGAINST POWDERY MILDEW

Cucumbers sensitive to powdery mildew were sprouted in trays and then transferred to pots of 16 cm diameter, two plants per pot. They were kept in a hothouse at 18° C.-25° C. at a relative humidity of 60%-70%. The cucumber plants were contaminated with powdery mildew collected from pumpkin leaves by passing the contaminated leaf over the leaves of the plants to be tested and the plants then sprayed with water. First treatment was with the first appearance of the disease, by spraying until dripping. All treatments were at a concentration of 0.03%, except for the commercial Myclobutanal (a systemic fungicide of Rohm and Haas Co.), where a concentration of 0.006% was used. The status of the disease was determined by three different people. The experiment was conducted in blocks, at random, with repetitions. Four blocks of four repetitions of ten treatments (total 160 pots) at three evaluation periods. The results appear in Table 2.

TABLE 2

DISEASE INDEX[a] OF CUCUMBERS INOCULATED WITH POWDERY MILDEW AND TREATED WITH FORMULATIONS OF VARIOUS METAL COMPLEXES OF PROCHLORAZ.

| | Disease Index Days After Treatment | |
|---|---|---|
| Active Compound | 7 | 14 |
| Myclobutanol | 1.34 A[d] | 0.81 B |
| SnCl$_2$ complex of Prochloraz | 1.97 AB | 0.78 B |
| ZnCl$_2$ complex of Prochloraz | 1.63 AB | 0.94 BC |
| CoCl$_2$ complex of Prochloraz | 2.06 B | 1.38 D |
| Octave[b] | 2.69 CD | 1.50 D |
| Control[c] | 4.44 E | 4.66 F |

[a] = Key: 0 = clean; 1 = 10%-20% sick; 2 = 20%-30% sick; 3 = 30%-40% sick; 4 = 40%-50% sick; 5 = over 50% sick.
[b] = Trademark for Boots' Mn(II)Cl$_2$ complex of prochloraz.
[c] = All ingredients of formulations except the active one.
[d] = Numbers followed by dissimilar letters within columns, are significantly different (P = 0.05).

EXAMPLE 8

FUNGICIDAL ACTIVITY OF THE ZINC COMPLEX AGAINST COFFEE BERRY DISEASE

The zinc complex of prochloraz was tested for its activity against coffee berry disease as follows:

Approximately 3.5 mm sections of colonized branches are washed in a solution of Teepol or similar wetting agent to remove any initial spore load. Sections are laid on moistened cellosine wadding in plastic boxes, 12 sections per box. Three boxes are sprayed with each concentration of the candidate material, closed and incubated for three days. After incubation the spores are removed by vigorous shaking of each of the 12 twigs in 10 ml water and are counted, using a haemocytometer slide. The sections of the branch are measured and their volume taken by displacement. The parameters measured were concentration of the formulation and expressed as percent active ingredient (A.I.) and percent inhibition of sporulation. The inhibition of sporulation was expressed in relation to the sporulation of unsprayed control and folpet as the standard fungicide. Each determination was done in triplicate and repeated at least three times. The dose response curves were analyzed by linear regression and the different formulations were compared at the 80% inhibition point. The results as they appear in Table 3 show the very good activity of the zinc complex of prochloraz, especially as compared to the results of known commercial metal complexes. Thus, the zinc complex shows activity against coffee berry disease more than two times greater than that shown for the commercial "Octave".

TABLE 3

INHIBITION OF COFFEE BERRY DISEASE BY THE ZINC COMPLEX OF PROCHLORAZ AND COMPARISON WITH THE ACTIVITY OF KNOWN METAL COMPLEXES OF PROCHLORAZ

| Active Compound | Per Cent Active Ingredient for for 80% Inhibition |
| --- | --- |
| ZnCl$_2$ complex of prochloraz | 0.09 |
| NiCl$_2$ complex of prochloraz | 0.12 |
| Octave[a] | 0.20 |
| Folpet | 0.62 |

[a] = Trademark of Boots Mn(II)Cl$_2$ complex of prochloraz.

We claim:

1. A crystalline metal complex of prochloraz having the formula:

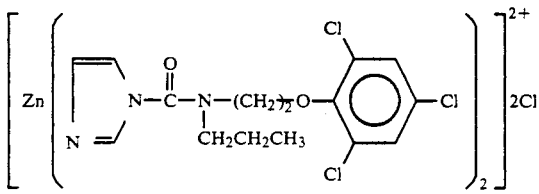

having a melting point of 100° C.–102° C.

2. A crystalline metal complex of prochloraz having the formula:

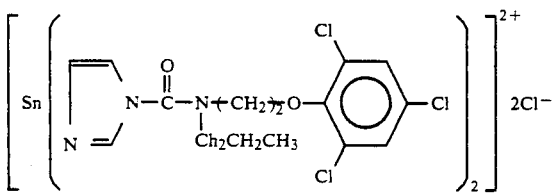

having a melting point of 95° C.

3. A fungicidal composition containing a solid or liquid diluent or carrier and a fungicidally effective amount of a crystalline metal complex of prochloraz having the formula

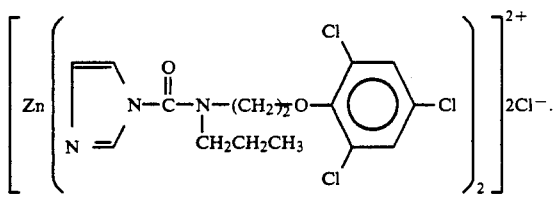

4. A fungicidal composition containing a solid or liquid diluent or carrier and a fungicidally effective amount of a crystalline metal complex of prochloraz having the formula:

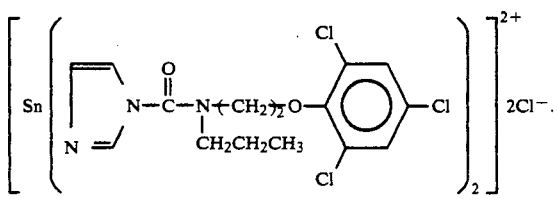

5. A fungicidal composition in accordance with claim 3 in the form of a wettable powder.

6. A method of controlling fungi which comprises applying to the infected material or plant a composition containing an effective amount of a crystalline complex of prochloraz in accordance with claim 1.

7. A method of controlling powdery mildew which comprises applying to the infected material or plant a composition containing an effective amount of a crystalline metal complex of prochloraz in accordance with claim 1.

8. A method of controlling coffee berry disease, which comprises applying to the infected material; or plant a composition containing an effective amount of a crystalline zinc complex of prochloraz in accordance with claim 1.

9. A fungicidal composition in accordance with claim 4 in the form of a wettable powder.

10. A method of controlling fungi which comprises applying to the infected material or plant a composition containing an effective amount of a crystalline complex of prochloraz in accordance with claim 2.

11. A method of controlling powdery mildew which comprises applying to the infected material or plant a composition containing an effective amount of a crystalline metal complex of prochloraz in accordance with claim 2.

* * * * *